United States Patent
Horlle et al.

(10) Patent No.: US 8,961,512 B2
(45) Date of Patent: Feb. 24, 2015

(54) ELECTROSURGICAL INSTRUMENT

(75) Inventors: Andreas Horlle, Berlin (DE); Timo Strauss, Berlin (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 1092 days.

(21) Appl. No.: 13/001,495

(22) PCT Filed: Jun. 29, 2009

(86) PCT No.: PCT/EP2009/058115
§ 371 (c)(1),
(2), (4) Date: Feb. 8, 2011

(87) PCT Pub. No.: WO2010/000697
PCT Pub. Date: Jan. 7, 2010

(65) Prior Publication Data
US 2011/0130757 A1     Jun. 2, 2011

(30) Foreign Application Priority Data
Jun. 30, 2008   (DE) .................... 10 2008 030 285

(51) Int. Cl.
*A61B 18/14*   (2006.01)
*A61B 17/29*   (2006.01)
(Continued)

(52) U.S. Cl.
CPC ..... *A61B 18/1445* (2013.01); *A61B 2017/2945* (2013.01); *A61B 2018/00011* (2013.01); *A61B 2018/00023* (2013.01); *A61B 2018/00345* (2013.01); *A61B 2018/00404* (2013.01);
(Continued)

(58) Field of Classification Search
USPC ...................................................... 606/45–52
See application file for complete search history.

(56) References Cited

U.S. PATENT DOCUMENTS 5,269,780 A * 12/1993 Roos ............................. 606/42
5,443,463 A    8/1995 Stern et al.
(Continued)

FOREIGN PATENT DOCUMENTS

WO   WO 99/23960 A1   5/1999
WO   WO 99/40861 A1   8/1999

OTHER PUBLICATIONS

Sep. 1, 2009 International Search Report issued in Application No. PCT/EP2009/058115.
(Continued)

*Primary Examiner* — Michael Peffley
(74) *Attorney, Agent, or Firm* — Oliff PLC

(57) ABSTRACT

An electrosurgical instrument having a distal end and a gripping device which is arranged at the distal end in the longitudinal direction and which includes at least a clamping jaw portion and a coagulation jaw portion. The coagulation jaw portion has a plurality of electrically separated coagulation electrodes which are substantially immovable relative to each other. At least one of the jaw portions is movable from an open position into a closed clamping position, wherein the jaw portions at least portion-wise engage into each other in the clamping position and are of such a configuration that the tissue can be clamped between the jaw portions substantially in a half-wave shape. The coagulation jaw portion has at least two electrode arrangements which are arranged at different sides and have respective electrically separated coagulation electrodes, by means of which the tissue is coagulatable in two substantially mutually separated coagulation regions.

15 Claims, 7 Drawing Sheets

(51) Int. Cl.
  *A61B 18/00* (2006.01)
  *A61B 18/12* (2006.01)
(52) U.S. Cl.
  CPC .................. *A61B2018/00601* (2013.01); *A61B 2018/00607* (2013.01); *A61B 2018/00619* (2013.01); *A61B 2018/0063* (2013.01); *A61B 2018/126* (2013.01); *A61B 2018/1432* (2013.01)
  USPC ............................................. 606/51; 606/49

(56) References Cited

U.S. PATENT DOCUMENTS

| | | | |
|---|---|---|---|
| 5,458,598 A | 10/1995 | Feinberg et al. | |
| 5,693,051 A | 12/1997 | Schulze et al. | |
| 5,891,141 A * | 4/1999 | Rydell | 606/45 |
| 5,964,758 A * | 10/1999 | Dresden | 606/45 |
| 6,126,658 A * | 10/2000 | Baker | 606/51 |
| 6,152,923 A | 11/2000 | Ryan | |
| 6,206,876 B1 | 3/2001 | Levine et al. | |
| 6,500,176 B1 | 12/2002 | Truckai et al. | |
| 6,520,960 B2 * | 2/2003 | Blocher et al. | 606/51 |
| 6,679,882 B1 | 1/2004 | Kornerup | |
| 6,770,072 B1 * | 8/2004 | Truckai et al. | 606/52 |
| 2007/0185487 A1 * | 8/2007 | Hafner | 606/45 |
| 2008/0015567 A1 | 1/2008 | Kimura | |
| 2008/0071268 A1 | 3/2008 | Hafner | |

OTHER PUBLICATIONS

Sep. 1, 2009 Written Opinion issued in PCT/EP2009/058115.
German Search Report issued in foreign counterpart application. No. 102008030285.6 dated Jan. 13, 2009 (with translation).

* cited by examiner

ELECTROSURGICAL INSTRUMENT

BACKGROUND

The invention concerns an electrosurgical instrument for the bipolar coagulation of biological tissue, comprising a distal end, a gripping device which is arranged at the distal end in the longitudinal direction and which includes at least a clamping jaw portion and a coagulation jaw portion, wherein the coagulation jaw portion has a plurality of electrically separated coagulation electrodes substantially immovable relative to each other, at least one of the jaw portions is adapted to be movable from an open position into a closed clamping position, and the jaw portions at least portion-wise engage into each other in the clamping position and are of such a configuration that the tissue can be clamped between the jaw portions substantially in a half-wave shape.

Electrosurgical instruments of the specified kind are known from the state of the art and described for example in WO 99/40861 A1 or WO 99/23960 A1.

SUMMARY

A very wide range of different electrosurgical procedures have already long been applied in medical technology. Thus for example tissue separation or tissue removal (electrotomy) by means of high-frequency energy has already been a routine procedure in surgery for decades. The tissue is caused to vaporise by the cutting electrode from which a spark discharge emanates, in the immediate area surrounding the cutting electrode, and small capillary vessels are immediately closed off so that almost blood-free tissue cutting is possible. That method is used in all surgical and other medical disciplines for tissue separation or tissue removal.

A further method which is established in surgery and other medical disciplines is electrosurgical sclerosing of tissue or arresting bleeding by means of high-frequency current. The instruments used for that purpose are often in the form of gripping instruments such as pincers or tweezers. The distal ends of conventional gripping elements generally have large-area planar electrodes which are generally at a different (bipolar) or more rarely the same (monopolar) potential. Both in the case of the monopolar and also the bipolar use of the gripping instrument the piece of tissue to be sclerosed or the part of the blood vessel to be closed off is disposed between the electrodes arranged at the distal end of both gripping limbs of the gripping instrument. In the monopolar procedure the high-frequency current flows between those electrodes and a return electrode which is fixed to the patient at another location, generally on the surface of the skin of the patient. In the bipolar procedure the high-frequency current flows between the two electrodes at the distal end of the gripping limbs of the gripping instrument.

Cutting by means of wire or lancette electrodes disposed at the end of a handle and coagulation with gripping instruments are the most wide-spread high-frequency surgical procedures.

By virtue of the small dimensions of endoscopic or laparoscopic instruments, disadvantageous lever relationships can have the result that the gripping instruments in the state of the art, when reasonable forces are involved at the gripping portion, can be difficult to close or can lead to fatigue on the part of the doctor. The result of this can be that, in the case of conventional tongs-like gripping devices, a larger gap remains at the tip of the gripping device than near the pivot. That problem occurs in particular when gripping large veins (about >5 mm) and bunches of tissue and becomes even worse if the grip is of an unfavourable configuration and as a result it is not possible to build up high forces at the jaw portion. However, even in the case of a grip portion which is well designed, it is technically not always possible to exert a force of just any desired magnitude on the jaw portions as the material strengths of the components also encounter their limits, when an excessively high level of force is involved. In many products in the state of the art, hardened steel is used for the jaw portions to limit flexing of the jaw portions.

If jaw surfaces of the gripping limbs, as in the case of conventional tongs-like gripping devices, are not parallel when heat-sealing off the veins, a larger gap occurs at the tip than near the pivot, as mentioned above. That results in lesser compression of the tissue at the tip of the gripping device and as a result also a lower degree of heating by virtue of the lower current density and a greater transfer resistance. That problem occurs in particular with large veins and thick bunches of tissue.

The instruments described in WO 99/40861 A1 and WO 99/23960 A1 try to resolve the specified problems by the jaw portions engaging into each other and thus clamping the tissue in a U-shape between the jaw portions, with a relatively uniform force, transversely with respect to the direction of movement, It has been found however that in part only irregular or inadequate tissue coagulation is achieved with the known instruments. Unreliable tissue coagulation can therefore represent a problem with the known instruments.

Therefore the problem of the invention is to provide a surgical instrument for the coagulation of biological tissue, which permits reliable coagulation of the tissue and ensures easy handling.

That problem is solved by the electrosurgical instrument set forth in the opening part of this specification, in that the coagulation jaw portion has at least two electrode arrangements which are arranged at different sides and have respective electrically separated coagulation electrodes, by means of which the tissue is coagulatable in two substantially mutually separated coagulation regions.

The solution according to the invention has the advantage that two comparably small tissue regions are coagulated in operation. It has been found that, in those small tissue regions, the factors which are important in respect of coagulation, temperature and pressure, are more easily controllable than in the large coagulation region involved with instruments in the state of the art. Thus, reliable tissue coagulation which is highly important for example when closing off a vein is ensured in the two coagulation regions.

As the coagulation electrodes on the coagulation jaw portion are arranged immovably relative to each other, short-circuits during coagulation are excluded. It is possible to dispense with structurally complicated and expensive spacers. The solution according to the invention is therefore structurally particularly simple and can be manufactured inexpensively.

Further advantageous configurations of the invention, which are independent of each other, are described in the appendant claims.

Thus the instrument according to the invention can have at least one electrosurgical cutting electrode for cutting the tissue and the cutting electrode can be so arranged that the tissue is severable between the coagulation regions. That has the advantage that the clamped tissue can be electrically severed therethrough with the coagulation instrument according to the invention. Particularly when closing off a vein the clamped vein can firstly be coagulated and then severed between the two coagulation regions. It has been found that cutting can be particularly well effected electrically in the tissue region between the coagulation regions. The tissue which is less coagulated in that region appears to be highly suited to electrosurgical cutting. The fact that the tissue is clamped in a half-wave shape provides that the tissue is pulled taut within the gripping device. It has been found that tissue which is pulled taut can be more easily electrosurgically severed.

The half wave-shaped gripping can be for example U-shaped, V-shaped or in the form of half a sine wave.

In addition the cutting electrode can extend over the entire length of a working region of the instrument, in which the tissue can be clamped and coagulated. In that way there is no need for a structurally complicated and expensive advance movement of the cutting element. The instrument according to the invention can thus be structurally simple and inexpensive to manufacture.

To be able to cut reliably in a bipolar mode with the instrument according to the invention, the active surface of the cutting electrode can be substantially smaller than the active surface of the coagulation electrodes so that in operation a flow of current is possible between the cutting electrode and the most closely adjacent coagulation electrodes. The coagulation electrodes which are further away from the cutting electrode can be electrically switched off in the cutting operation in order not to deflect the flow of current. In that way the cutting current flow does not have an adverse influence on vein closure, that is to say the risk of an arc being fired at the remote coagulation electrodes and severing unwelded tissue is excluded.

In a further advantageous configuration the cutting element can be provided at the coagulation jaw portion and the coagulation jaw portion can be substantially immovably coupled to the distal end of the instrument. That has the advantage that the coagulation electrodes and the cutting electrode are arranged at the same jaw portion and that jaw portion is rigidly connected to the shank of the instrument. In that way there is no need for movable electrical connections to supply the electrode with HF energy. In that fashion the instrument according to the invention can be of a structurally simple design and is inexpensive to manufacture.

In a further embodiment the coagulation jaw portion can include two coagulation electrodes which extend parallel and which provide the electrode arrangements and which at least portion-wise enclose the clamping jaw portion in the longitudinal direction of the instrument. The tissue which is not received in the gripping device can also be coagulated with the coagulation end provided in that way. Thus for example it is possible to stop relatively minor bleeds with the instrument according to the invention by simply touching same with the coagulation end.

To increase the pressure on the clamped tissue the coagulation electrodes and/or the clamping jaw portion can have clamping surfaces which are round or curved in cross-section. The round clamping surfaces exert a maximum of pressure on the tissue, in a line-shaped region. As high pressure affords good coagulation, tissue coagulation is particularly good in the line-shaped region.

The pressure on the tissue at the coagulation electrodes can be further increased if in the clamping position the gap between the jaw portions in the working region in which the tissue can be clamped and coagulated is less than 1 mm. Furthermore it is also possible to produce the instrument substantially without a gap between the jaw portions, which further increases the clamping force on the tissue. Due to the small or no gap, the gripped tissue urges the jaw portions away from each other more vigorously so that the closing force is increased.

In another advantageous development rib elements extending transversely with respect to the longitudinal direction can be provided at at least one of the jaw portions. The rib elements prevent gripped clamped tissue from slipping out of the gripping device.

To prevent excessively great heating of the tissue in operation of the instrument the coagulation jaw portion can have an inwardly disposed lumen through which a fluid can flow for cooling the coagulation electrodes and/or the cutting electrode.

Besides the specified electrosurgical instrument and its above-specified embodiments the invention further concerns a method of bipolar coagulation of biological tissue, wherein firstly the tissue is clamped substantially in a half wave-shape between a clamping jaw portion and a coagulation jaw portion of an electrosurgical instrument and then the tissue is coagulated by means of at least two electrode arrangements in two substantially mutually separated coagulation regions. In addition in an advantageous device of the method the clamped coagulated tissue can be electrically severed between the separated coagulation regions.

BRIEF DESCRIPTION OF THE DRAWINGS

The invention is described hereinafter with reference to the accompanying drawings in which.

DETAILED DESCRIPTION OF EMBODIMENTS

The invention is described hereinafter by means of embodiments by way of example.

Figure 1:
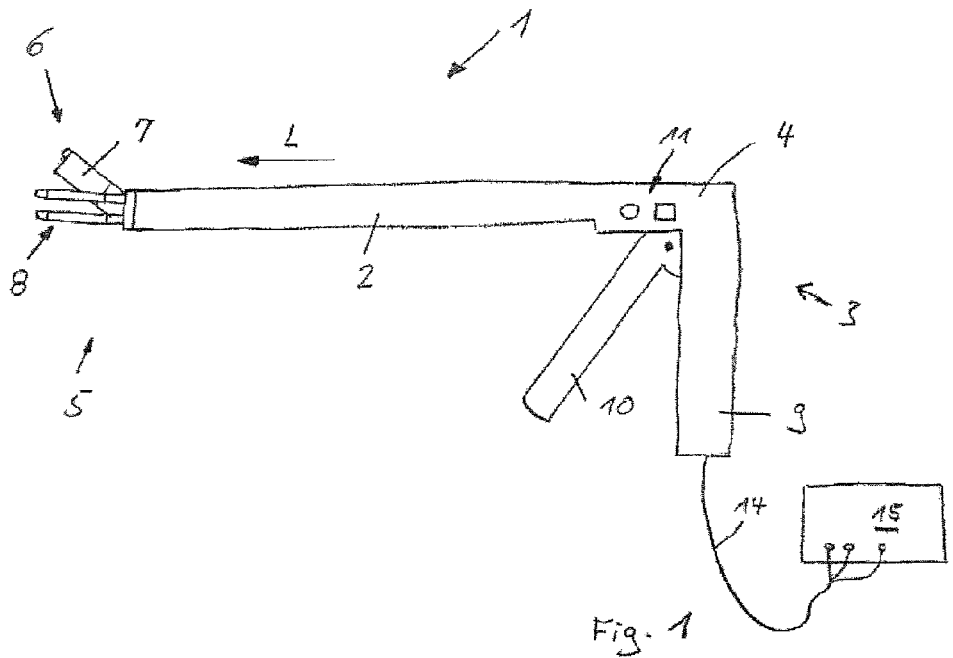
FIG. 1 shows a diagrammatic view of an embodiment by way of example of an electrosurgical instrument according to the invention.

FIG. 1 is a highly diagrammatic view of an embodiment by way of example of an electrosurgical instrument 1 according to the invention for the coagulation of biological tissue. The instrument 1 which is designed for laparoscopic or endoscopic uses includes an elongate shank 2, a handle portion 4 arranged at the proximal end 3 of the shank 2 and a gripping device 6 adjoining the distal end 5 on the shank 2.

The gripping device 6 has a clamping jaw portion 7 and a coagulation jaw portion 8. FIG. 1 shows the gripping device 6 in an open position in which the jaw portions 7, 8 are opened to receive tissue. The gripping device 6 is described in greater detail hereinafter.

As the instrument 1 is designed for laparoscopic or endoscopic use the round cross-section of the shank 2 is of an outside diameter of about 5 mm. The dimensions of the gripping device 6 also do not project beyond that diameter in the closed position so that the instrument can be introduced into the body of a patient for example through a trocar. It will be appreciated that other designs of other diameters such as for example 10 mm are possible.

The handle portion 4 which serves for gripping and operation of the instrument 1 by the doctor has a fixed grip portion 9 and a movable grip portion 10. The grip portion 10 is coupled to the clamping jaw portion 7 so that the clamping jaw portion 7 is movable by means of the grip portion 10. In addition, provided on the handle portion 4 are two on/off switches 11 by which the coagulation operation and/or the cutting operation can be started or stopped. Electrical connecting lines and necessary mechanical connecting elements extend in the interior of the hollow shank 2. The handle portion 4 is only illustrated highly diagrammatically and can alternatively be of any suitable shape known from the state of the art.

The instrument 1 is connected to a high-frequency generator 15 by way of electrical connecting lines 14. The high-frequency generator 15 generates a high-frequency energy suitable for operation of the instrument according to the invention.

Figure 2:
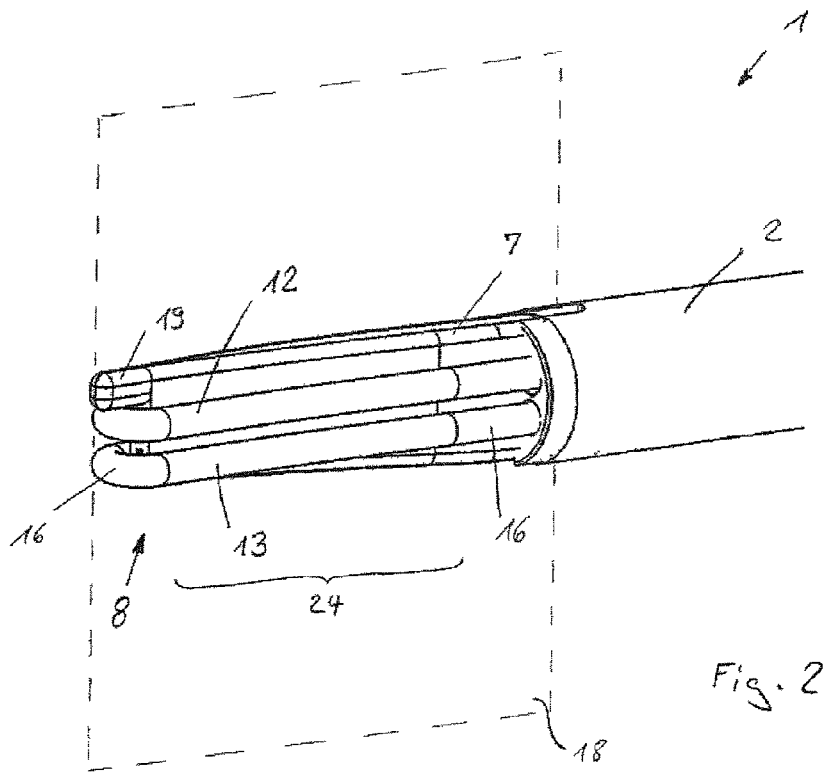
FIG. 2 shows an enlarged diagrammatic view of the distal end of the instrument of FIG. 1 in a closed clamping position.
Figure 3:
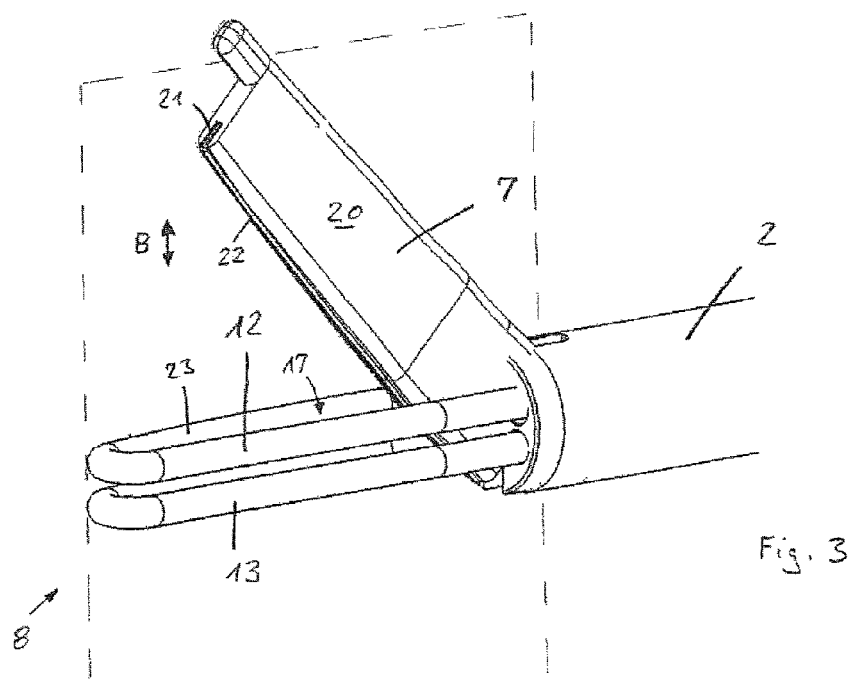
FIG. 3 shows an enlarged diagrammatic view of the distal end of the instrument of FIG. 1 in an open position.

FIGS. 2 and 3 show the distal end 5 of the instrument 1 of FIG. 1 on an enlarged scale, FIG. 2 showing the gripping device 6 in a closed clamping position and FIG. 3 showing it in an open position. The configuration according to the invention of the gripping device 6 will now be described in greater detail with reference to FIGS. 2 and 3, In the embodiment by way of example shown in FIGS. 2 and 3 the coagulation jaw portion 8 includes two coagulation electrodes 12, 13 which extend substantially parallel. The coagulation electrodes 12, 13 are in the form of round electrodes of round cross-section. Other cross-sectional shapes are however possible. On both sides of the clamping jaw portion 7 the coagulation electrodes 12, 13 open in the longitudinal direction L out of the distal end of the shank 2. In the clamping position in FIG. 2 the coagulation electrodes 12, 13 extend substantially parallel to each other on both sides of the clamping jaw portion 7 in the longitudinal direction L and at a substantially equal spacing relative to the clamping jaw portion 7. At the distal end of the instrument 1 the coagulation electrodes 12, 13 embrace the clamping jaw portion 7. Thus the coagulation electrodes 12, 13 each form a respective elongate receiving window 17 into which the clamping jaw portion 7 engages in the closed clamping position of FIG. 2. The jaw portions 7, 8 engage into each other in the closed clamping position.

The coagulation electrodes 12, 13 are connected substantially fixedly and non-pivotably to the shank 2. In the interior of the shank 2 the electrically mutually separated coagulation electrodes 12, 13 are respectively connected to one of the electrical connecting lines 14 by way of which the coagulation electrodes 12, 13 are electrically coupled to different poles of the high-frequency generator 15. In the distal and proximal regions the coagulation electrodes are surrounded by an electrical insulator 16. In the embodiment of FIGS. 2 and 3 the insulator 16 is in the form of a plastic material coating. It will be appreciated that other configurations such as for example a ceramic enclosure are possible. In a working region 24 of the instrument 1 the coagulation electrodes 12, 13 are not covered by the insulator 16 and thus the tissue can be coagulated in the working region 24.

In operation of the instrument 1 according to the invention a bipolar ac voltage is applied between the two electrodes 12, 13, by which the tissue connected to the coagulation electrodes 12, 13 in the working region 24 can be coagulated. A short-circuit by touching of the coagulation electrodes 12, 13 is precluded on the one hand by the fact that they are immovably connected to the shank 2 and on the other hand by manufacture thereof from an only slightly elastic material such as for example high-quality steel.

The clamping jaw portion 7 which is engaged between the coagulation electrodes 12, 13 in the closed position is movably connected to the shank 2 by way of a rotary pivot. In that way the clamping jaw portion 7 can be pivoted in a direction of movement B from the closed position in FIG. 2 into the open position in FIG. 3. The clamping jaw portion 7 is connected to the shank 2 in such a way that it moves within a plane of movement 18 extending in the longitudinal direction L. The clamping jaw portion 7 is connected to the movable grip portion 10 of the handle portion 4 by way of mechanical connecting elements (not shown) extending in the interior of the shank 2. An abutment 19 projecting in a nose-shaped configuration in the longitudinal direction L limits the movement of the clamping jaw portion 7 in a direction towards the closed position. It will be appreciated that the abutment 19 can also be provided at another location and/or of a different shape.

The clamping jaw portion 7 is here in the form of a substantially rectangular plate having lateral clamping surfaces 20 extending parallel and with rounded edges. At the underside which faces in the direction of movement B towards the coagulation jaw portion 8 the clamping jaw portion 7 has a cutting electrode 21. In the embodiment of FIGS. 2 and 3 the cutting electrode 21 extends over the entire length of the clamping jaw portion 7 and over the entire length of the working region 24. In the embodiment of FIGS. 2 and 3 the cutting electrode 21 is of a rectangular cross-section and is fitted into a groove in the clamping jaw portion 7. The cutting electrode 21 is pressed or glued into the groove for fixing it. In that situation the cutting electrode 21 is inserted in such a way that only a small part protrudes from the groove. Therefore the exposed active surface 22 of the cutting electrode 21 is substantially smaller than the active surface 23 of the coagulation electrodes 12, 13.

The cutting electrode 21 is connected to the high-frequency generator 15 by a further connecting line 14 extending in the interior of the shank 2.

Figure 10:
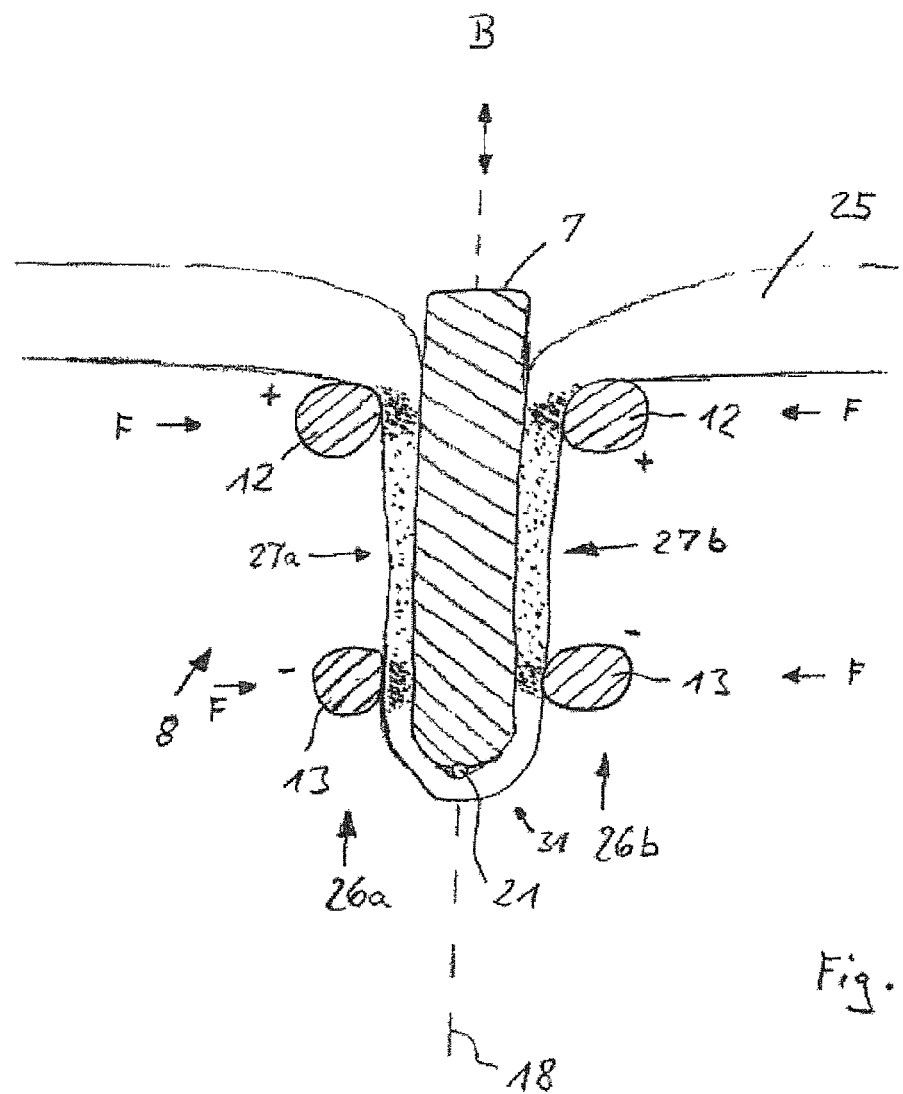
FIG. 10 shows a diagrammatic view in section of a further embodiment of the instrument according to the invention with gripped tissue.

The mode of operation of the embodiment of FIGS. 2 and 3 is described hereinafter by reference to the diagrammatic view in FIG. 10. FIG. 10 shows a similar instrument 1 to that shown in FIG. 2. The only difference in relation to the FIG. 2 instrument is that the cutting electrode 21 in FIG. 10 is in the form of a wire electrode of round cross-section. The functions described hereinafter are the same. FIG. 10 shows the instrument 1 in section in the closed clamping position in which tissue 25, for example a vein, is clamped in the working region 24 between the jaw portions 7, 8 in a half wave-shaped configuration, in particular in a U-shape. In order to move into the closed clamping position the instrument is firstly moved into the open position and the tissue 25 is enclosed with the opened gripping device 6. By actuation of the movable grip portion 10 the gripping device moves into the closed position and in so doing grips the tissue 25 and clamps it in a half wave-shape between the jaw portions 7, 8.

The way in which the jaw portions 7, 8 engage into each other is clearly visible in FIG. 10. In the movement from the open position into the closed clamping position the clamping jaw portion 7 engages progressively further into the coagulation jaw portion 8. In the closed clamping position the lower edge of the clamping jaw portion 7 has moved beyond the lower edge of the coagulation electrode 13 and projects beyond it. That arrangement provides that the tissue 25 is clamped substantially in a U-shape in the closed clamping position between the jaw portions 7, 8. The tissue 25 is pushed by the clamping jaw portion 7 into the receiving window 17 between the coagulation electrodes 12, 13 and in that case folded in a rectangular shape or a U-shape, that is to say the tissue 25 is drawn taut around the clamping jaw portion 7. The U-shape or rectangular shape is due to the external shape of the clamping jaw portion 7 which in this embodiment is of a rectangular external contour. When the clamping jaw portion is pushed in, the coagulation electrodes 12, 13 are urged away from each other transversely with respect to the direction of movement B by the stack consisting of the tissue 25 and the clamping jaw portion 7. When that happens the taut tissue 25 is additionally compressed so that for example in the case of a vein blood is urged out of the coagulation regions 27a, 27b.

The coagulation electrodes 12, 13 which are substantially immovable relative to each other form respective electrode arrangements 26a, 26b on both sides of the clamping jaw portion 7 and on both sides of the plane of movement 18. Each electrode arrangement 26a, 26b has electrically separated coagulation electrodes 12, 13 at differing potential. In order better to illustrate the opposite potentials, associated with the coagulation electrode 12 is a plus sign + while associated with the coagulation electrode 13 is a minus sign –, although it will be appreciated that the instrument 1 is operated with an ac voltage with which the polarity constantly reverses. In the case of bipolar coagulation the current flows within the two electrode arrangements 26a, 26b between the coagulation electrodes 12, 13. Accordingly the gripped tissue 25 is coagulated in two mutually separated coagulation regions 27a, 27b. The tissue 25 is not coagulated or is at least less coagulated in a cutting region 31 between the coagulation regions 27a, 27b, than in the coagulation regions 27a, 27b, as here there is no or little flow of current. The electrode arrangements 26a, 26b are provided on both sides of the plane of movement 18.

The coagulation electrodes 12, 13 are so arranged that, in the clamping position without gripped tissue 25, they are at a very small or no spacing relative to the clamping jaw portion 7. When tissue 25 is clamped for coagulation purposes as in FIG. 10, the coagulation electrodes 12, 13 are urged outwardly away from the clamping jaw portion 7 transversely with respect to the direction of movement B. When tissue 25 is clamped, the coagulation electrodes 12, 13 which are elastically deformed in that way push back in the direction of the clamping jaw portion 7 and generate a pressure force F applied to the tissue 25. It has been found that that pressure force F acting transversely with respect to the direction of movement B positively influences the coagulation result. Therefore, in the tissue regions around the coagulation electrodes 12, 13 on which the pressure force F acts, the tissue 25 is coagulated to a greater degree than in the other regions. The round or curved clamping surfaces of the coagulation electrodes 12, 13 with which the tissue 25 is pressed against the clamping jaw portion 7 provide that the pressure area is small. The small pressure area additionally leads to an advantageous increase in the pressure force F.

After the tissue 25 is coagulated in the coagulation regions 27a, 27b, it can be severed in the cutting region 31 where the cutting electrode 21 is also provided, between the two coagulation regions 27a, 27b. For that purpose a suitable high-frequency voltage is applied between the cutting electrode 21 and the most closely adjacent coagulation electrode 13. Thereupon an arc fires at the cutting electrode 21 and severs the tissue. The arc is formed at the cutting electrode 21 and not at the coagulation electrode 13 because the current density is substantially greater at the substantially smaller active surface 22 of the cutting electrode 21. With the instrument 1 according to the invention the electrode arrangements 26a, 26b are so placed that they do not coagulate or only little coagulate the tissue 25 in the cutting region 31.

A further embodiment of the instrument 1 according to the invention is described hereinafter with reference to FIGS. 4 to 6. For the sake of simplicity it is only the differences in relation to the above-described embodiments that will be considered here.

Figure 4:
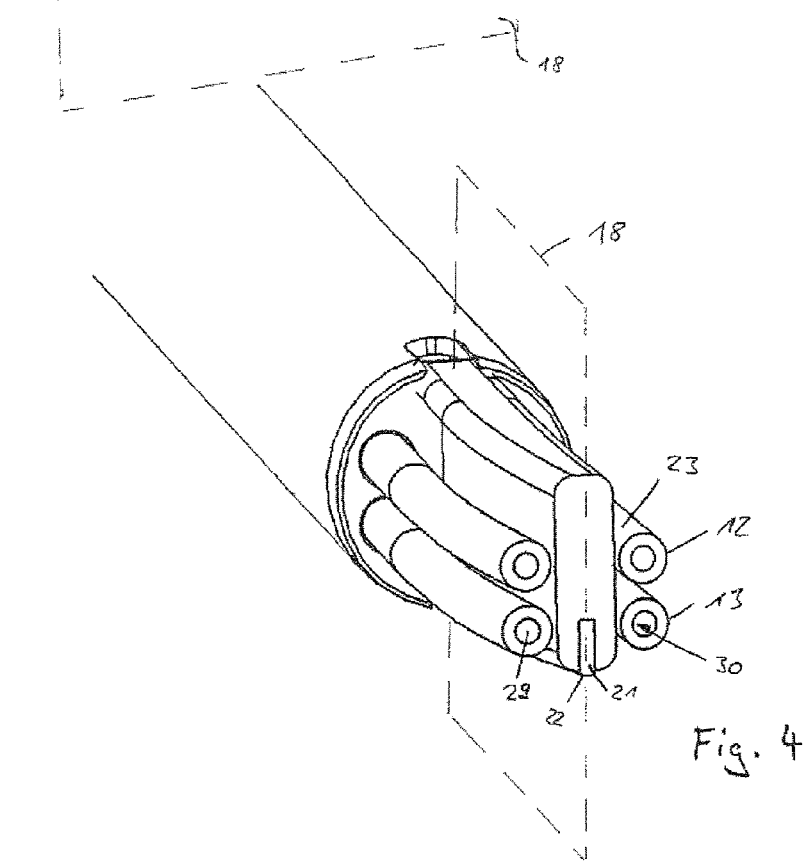
FIG. 4 shows a diagrammatic view in section of the instrument of FIG. 5.
Figure 5:
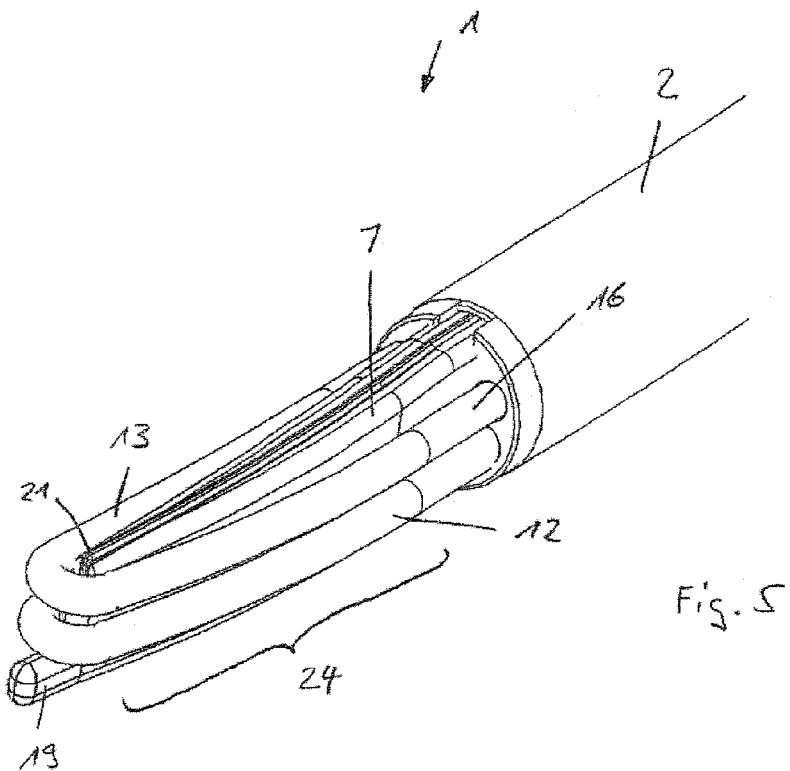
FIG. 5 shows a diagrammatic view of the distal end of a further embodiment of an instrument according to the invention from below.
Figure 6:
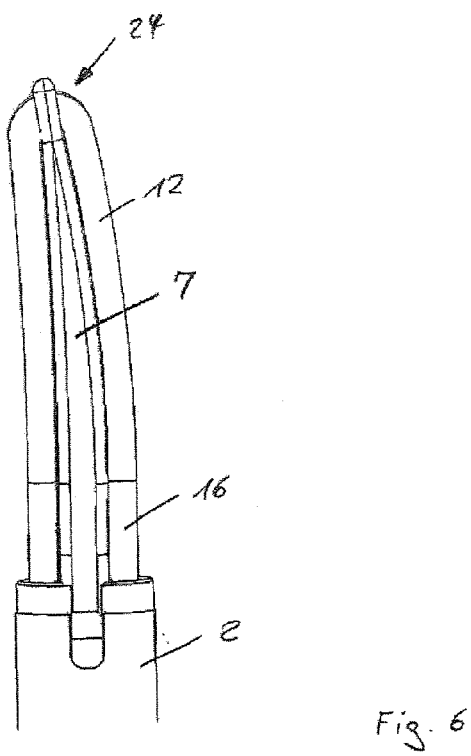
FIG. 6 shows a plan view of the instrument of FIG. 5.

As a distinction in relation to the above-described embodiments the instrument 1 in FIGS. 4 to 6 is in the form of what is referred to as a Maryland design. In other words the jaw portions 7, 8 are curved uniformly to one side, which has the advantage, particularly in endoscopic use, that the doctor can better see the distal end of the curved gripping device 6 when viewing through the endoscope. The invention is particularly suitable for the Maryland design because the cutting electrode 21 which extends over the entire length of the working region 24 can be arranged immovably. Accordingly no advance movement is necessary, the implementation of which is often problematical with instruments in the state of the art.

Furthermore the insulator 16 in FIGS. 4 to 6 is arranged only in the proximal region of the coagulation electrodes 12, 13. The distal region of the coagulation electrodes 12, 13 is not insulated and forms a coagulation end 28 of the instrument 1. The coagulation end 28 can be used by the doctor for bipolar coagulation even of tissue which is not gripped.

As FIG. 4 shows the coagulation electrodes 12, 13 each have a respective lumen 29 in their interior. The lumen 29 can be flushed through with a suitable cooling fluid to cool the coagulation electrodes in operation. Disposed at the inside wall of the lumen 29 is an electrical insulating layer 30 so that the cooling fluid does not cause a short-circuit.

A further embodiment of the instrument 1 according to the invention is described hereinafter with reference to FIGS. 7 and 8. For the sake of simplicity it is only the differences in relation to the above-described embodiments that will be considered here.

Figure 7:
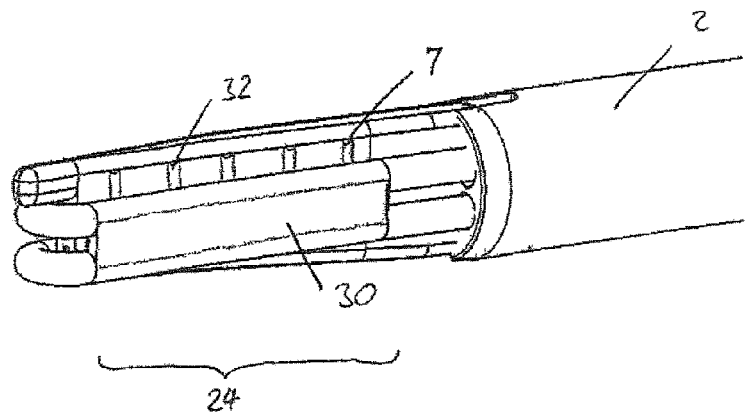
FIG. 7 shows a diagrammatic view of the distal end of a further embodiment of an instrument according to the invention.
Figure 8:
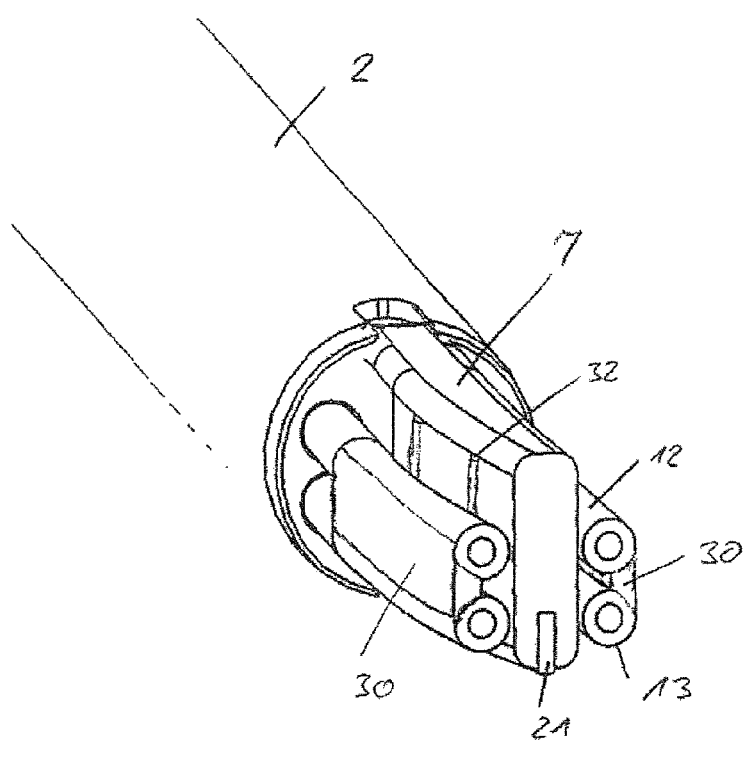
FIG. 8 shows a diagrammatic view in section of the distal end of a further embodiment of an instrument according to the invention.

As a difference in relation to the above-described embodiments in the instrument 1 in FIGS. 7 and 8 electrically insulating spacers 30 are arranged between the coagulation electrodes 12, 13 in the working region 24. The spacers 30 can be made for example from a suitable plastic material and fix the coagulation electrodes 12, 13 relative to each other. In that way a short-circuit due to the electrode surfaces touching can be even more reliably precluded.

In addition the clamping jaw portion 7 has rib elements 32 which are arranged transversely with respect to the longitudinal direction and which project outwardly in the direction of the coagulation electrodes 12, 13. Tissue 25 can be better held in the gripping device 6 by the rib elements 32.

A further embodiment of the instrument 1 according to the invention is described hereinafter with reference to FIG. 9. For the sake of simplicity it is only the differences in relation to the above-described embodiments that will be considered here.

Figure 9:
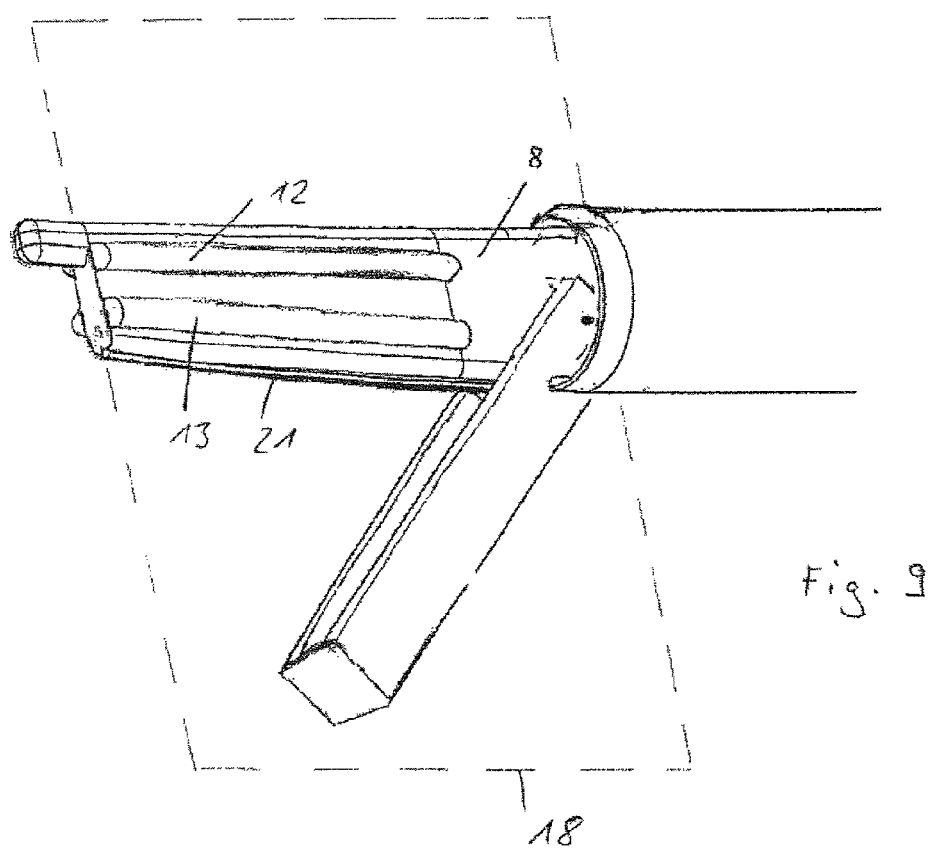
FIG. 9 shows a diagrammatic view of the distal end of a further embodiment of an instrument according to the invention.

As a difference in relation to the above-described embodiments in the instrument 1 in FIG. 9 the stationary coagulation jaw portion 8 is arranged within the movable clamping jaw portion 7. In addition the cutting electrode 21, like the coagulation electrodes 12, 13, is provided on the coagulation jaw portion 8. That has the advantage that all parts to be supplied with current are arranged on the same stationary jaw portion 8 and therefore no HF-energy has to be passed to moving parts. The coagulation electrodes 12, 13 which are of a half-round configuration are fitted on the coagulation jaw portion 8 which is otherwise made from an electrically insulating material.

A further embodiment of the instrument 1 according to the invention is described hereinafter with reference to FIG. 11. For the sake of simplicity it is only the differences in relation to the above-described embodiments that will be considered here.

Figure 11:
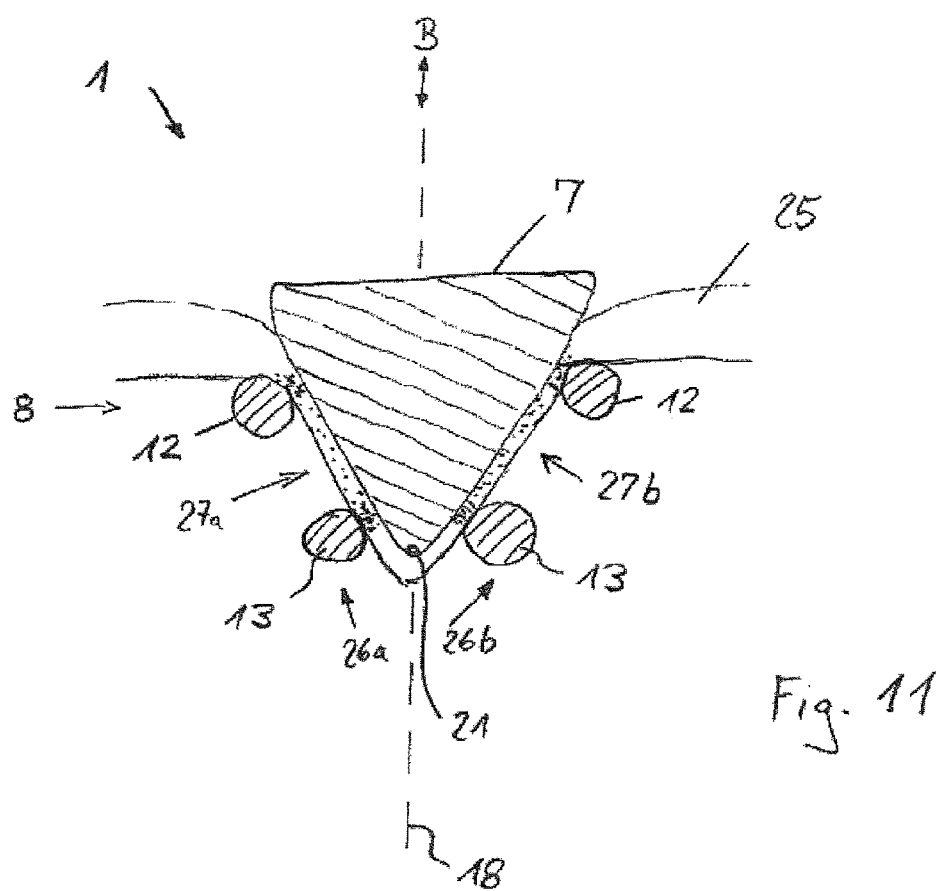
FIG. 11 shows a diagrammatic view in section of a further embodiment of the instrument according to the invention with gripped tissue.

FIG. 11 shows the instrument 1 in section in the closed clamping position in which tissue 25, for example a vein, is clamped in a V-shape in the working region 24 between the jaw portions 7, 8. As a difference in relation to the above-described embodiments the instrument 1 according to the invention shown in FIG. 11 has a wedge-shaped, that is to say V-shaped, clamping jaw portion 7. The two coagulation electrodes 12, 13 of the coagulation jaw portion 8 are arranged in correspondingly complementary relationship with the clamping surfaces of the clamping jaw portion 7 so that the tissue 25 is clamped in a V-shape. The cutting electrode 21 is placed at the tip of the wedge-shaped clamping jaw portion 7, at which the tissue is most greatly tensioned in the clamped condition and thereby can be particularly easily severed. The wedge-shaped clamping jaw portion 7 which, besides a force component in the direction of movement B, also presses against the coagulation electrodes 12, 13 with a force component transversely with respect to the direction of movement B provides that the tissue can be particularly easily gripped. Therefore the doctor can also use the instrument of this embodiment at the same time as a simple gripping instrument. That has the advantage that the doctor does not have to change the instrument if he needs a gripping instrument.

The invention claimed is:

1. An electrosurgical instrument for bipolar coagulation of biological tissue, the instrument comprising:
a distal end;
a gripping device which is arranged at the distal end in a longitudinal direction of the instrument and which includes at least a clamping jaw portion and a coagulation jaw portion, wherein
the coagulation jaw portion has a plurality of electrically separated coagulation electrodes substantially immovable relative to each other,
at least one of the clamping jaw portion and the coagulation jaw portion is configured to move from an open position into a closed clamping position, and
the clamping jaw portion and the coagulation jaw portion at least portion-wise engage into each other in the closed clamping position and are configured such that the tissue can be clamped between the clamping jaw portion and the coagulation jaw portion substantially in a half-wave shape,
wherein the coagulation jaw portion has at least two electrode arrangements which are both arranged at first and second different sides of the clamping jaw portion and have respective ones of the electrically separated coagulation electrodes, by which the tissue is coagulatable in two substantially mutually separated coagulation regions, and
wherein in the closed clamping position. (i) the coagulation electrodes extend substantially parallel to each other on the first side of the clamping jaw portion in the longitudinal direction, (ii) the coagulation electrodes extend substantially parallel to each other on the second side of the clamping jaw portion in the longitudinal direction, and (iii) the coagulation electrodes are arranged at a substantially equal spacing relative to the clamping jaw portion.

2. The electrosurgical instrument according to claim 1 wherein the instrument has at least one electrosurgical cutting electrode for cutting the tissue and the cutting electrode is so arranged that the tissue is severable between the coagulation regions.

3. The electrosurgical instrument according to claim 2 wherein the cutting electrode extends over the entire length of a working region of the instrument, in which the tissue can be clamped and coagulated.

4. The electrosurgical instrument according to claim 2, wherein an active surface of the cutting electrode is substantially smaller than active surfaces of the coagulation electrodes so that in operation bipolar cutting is possible with a flow of current between the cutting electrode and most closely adjacent ones of the coagulation electrodes.

5. The electrosurgical instrument according to claim 2, wherein the cutting element is arranged at the coagulation jaw portion and the coagulation jaw portion is arranged substantially immovably at the distal end of the instrument.

6. The electrosurgical instrument according to claim 2, wherein the coagulation jaw portion has an inwardly disposed lumen through which a fluid can flow for cooling the coagulation electrodes and/or the cutting electrode.

7. The electrosurgical instrument according to claim 1, wherein the coagulation jaw portion includes two coagulation electrodes which extend parallel and which provide both electrode arrangements and which at least portion-wise enclose the clamping jaw portion in the longitudinal direction of the instrument and thus form a distal coagulation end of the instrument.

8. The electrosurgical instrument according to claim 1, wherein the coagulation electrodes and/or the clamping jaw portion have clamping surfaces which are round or curved in cross-section.

9. The electrosurgical instrument according to claim 1, wherein, in the closed clamping position, a gap between the clamping jaw portion and the coagulation jaw portion in a working region in which the tissue can be clamped and coagulated is less than 1 mm.

10. The electrosurgical instrument according to claim 1, wherein rib elements extending transversely with respect to the longitudinal direction are provided at least at one of the clamping jaw portion and the coagulation jaw portion.

11. A method of performing bipolar coagulation of biological tissue, the method comprising:
clamping the biological tissue between a clamping jaw portion and a coagulation jaw portion of an electrosurgical instrument, the clamping jaw portion having first and second sides extending in a longitudinal direction of the electrosurgical instrument;
forming two substantially mutually separated coagulation regions in the biological tissue by the clamping, wherein coagulation electrodes of the coagulation jaw portion (i) extend substantially parallel to each other on the first side of the clamping jaw portion in the longitudinal direction. (ii) extend substantially parallel to each other on the second side of the clamping jaw portion in the longitudinal direction, and (iii) are arranged at a substantially equal spacing relative to the clamping jaw portion;

controlling a temperature and a pressure in the clamped biological tissue by ensuring that the substantially mutually separated coagulation regions are comparably small; and coagulating the biological tissue by of at least two electrode arrangements in the two substantially mutually separated coagulation regions in the biological tissue.

12. The method according to claim 11, wherein the biological tissue is clamped substantially in a half wave-shape.

13. A method of performing bipolar coagulation of biological tissue, the method comprising:

clamping the biological tissue between a clamping jaw portion and a coagulation jaw portion of an electrosurgical instrument, the clamping jaw portion having first and second sides extending in a longitudinal direction of the electrosurgical instrument; and coagulating the biological tissue by at least two electrode arrangements of the coagulation jaw portion in two substantially mutually separated coagulation regions, wherein coagulation electrodes of the at least two electrode arrangements (i) extend substantially parallel to each other on the first side of the clamping jaw portion in the longitudinal direction, (ii) extend substantially parallel to each other on the second side of the clamping jaw portion in the longitudinal direction. and (iii) are arranged at a substantially equal spacing relative to the clamping jaw portion.

14. The method according to claim 13, wherein the biological tissue is clamped substantially in a half wave-shape.

15. The method according to claim 13, further comprising:

electrically severing the clamped coagulated biological tissue in a location between the substantially mutually separated coagulation regions.

* * * * *